US006669908B2

(12) United States Patent
Weyker et al.

(10) Patent No.: US 6,669,908 B2
(45) Date of Patent: Dec. 30, 2003

(54) URINE TEST DEVICE

(75) Inventors: Daniel C. Weyker, San Diego, CA (US); Alan Fujii, Newport Beach, CA (US); John K. Zeis, San Marcos, CA (US); Thomas J. Marcello, Corona, CA (US); Veronica Terrazas, San Diego, CA (US); Lorraine C. Cogan, San Diego, CA (US)

(73) Assignee: Applied Biotech, Inc., San Diego, CA (US)

( * ) Notice: Subject to any disclaimer, the term of this patent is extended or adjusted under 35 U.S.C. 154(b) by 125 days.

(21) Appl. No.: 09/916,218

(22) Filed: Jul. 25, 2001

(65) Prior Publication Data

US 2003/0021727 A1 Jan. 30, 2003

(51) Int. Cl.[7] .............................................. G01N 21/00
(52) U.S. Cl. .............................. 422/58; 422/50; 422/55; 422/56; 422/61; 422/68.1; 422/99; 422/101; 422/102; 436/169; 436/164
(58) Field of Search ............................. 422/55, 50, 58, 422/61, 68.1, 69, 99, 101, 102, 104; 436/169, 164

(56) References Cited

U.S. PATENT DOCUMENTS

| 4,109,530 | A | | 8/1978 | Kim | |
|---|---|---|---|---|---|
| 4,473,530 | A | | 9/1984 | Villa-Real | |
| 4,690,801 | A | | 9/1987 | Anderson | |
| 4,852,560 | A | | 8/1989 | Hermann, Jr. et al. | 128/762 |
| 4,859,610 | A | * | 8/1989 | Maggio | 436/518 |
| 4,927,605 | A | | 5/1990 | Dorn et al. | |
| 5,403,551 | A | | 4/1995 | Galloway et al. | |
| 5,429,804 | A | | 7/1995 | Sayles | |
| 5,501,837 | A | | 3/1996 | Sayles | |
| 5,591,401 | A | | 1/1997 | Sayles | |
| 5,656,502 | A | | 8/1997 | MacKay et al. | 436/180 |
| 5,739,041 | A | | 4/1998 | Nazareth et al. | 436/518 |
| 5,785,044 | A | | 7/1998 | Meador et al. | 128/760 |
| 5,882,600 | A | | 3/1999 | Davis | |
| 5,897,840 | A | | 4/1999 | Owens, Jr. et al. | |
| 5,976,895 | A | | 11/1999 | Cipkowski | |
| 6,074,606 | A | | 6/2000 | Sayles | |
| 6,168,758 | B1 | | 1/2001 | Forsberg et al. | |
| 6,277,646 | B1 | | 8/2001 | Guirguis et al. | 436/165 |
| 6,342,183 | B1 | * | 1/2002 | Lappe et al. | 422/58 |
| 6,514,461 | B1 | | 2/2003 | Lappe et al. | 422/68.1 |
| 2002/0048819 | A1 | * | 4/2002 | Alley | 436/169 |
| 2003/0021736 | A1 | * | 1/2003 | Jemo | 422/58 |

* cited by examiner

*Primary Examiner*—Jill Warden
*Assistant Examiner*—Sam P. Siefke
(74) *Attorney, Agent, or Firm*—Fitch, Even, Tabin & Flannery

(57) ABSTRACT

A device for collecting, testing and transporting a liquid specimen of urine or the like incorporates a cup or container and a cooperating lid which becomes sealed about its upper rim when the lid is mated with the specimen-containing cup. An upwardly open subchamber of defined volume, formed in the bottom wall of the cup, is sealed by engagement with a downwardly extending hollow plug portion of the lid that has a bottom wall containing a central aperture closed by a frangible sheet material seal. When initial testing is to be conducted, an elongated assay cartridge is inserted vertically downward through the hollow plug. The bottom end splits open the frangible seal and enters into the subchamber containing the defined volume of the liquid sample, which becomes totally absorbed by a pair of elongated nitrocellulose strips, along which the liquid moves by capillary action to effect the assay tests.

18 Claims, 6 Drawing Sheets

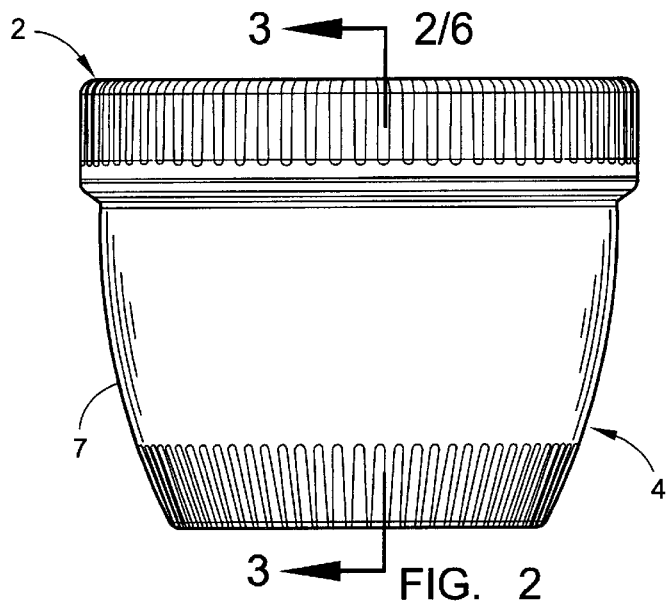
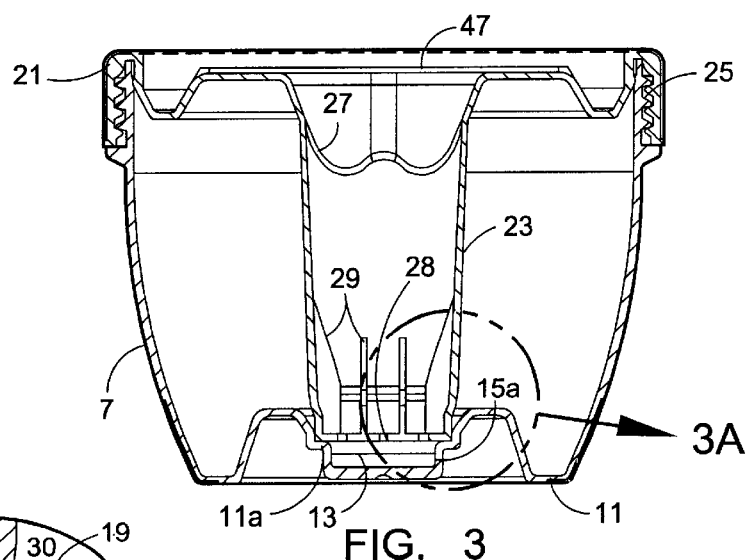
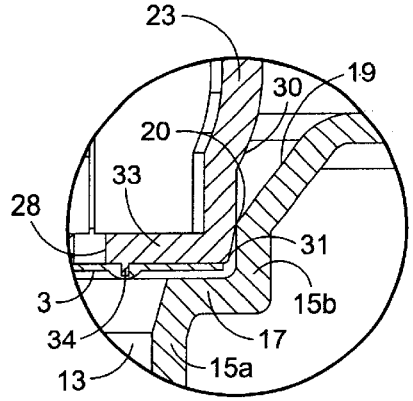
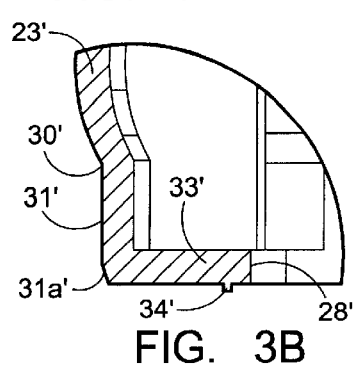
FIG. 2
FIG. 3
FIG. 3A
FIG. 3B

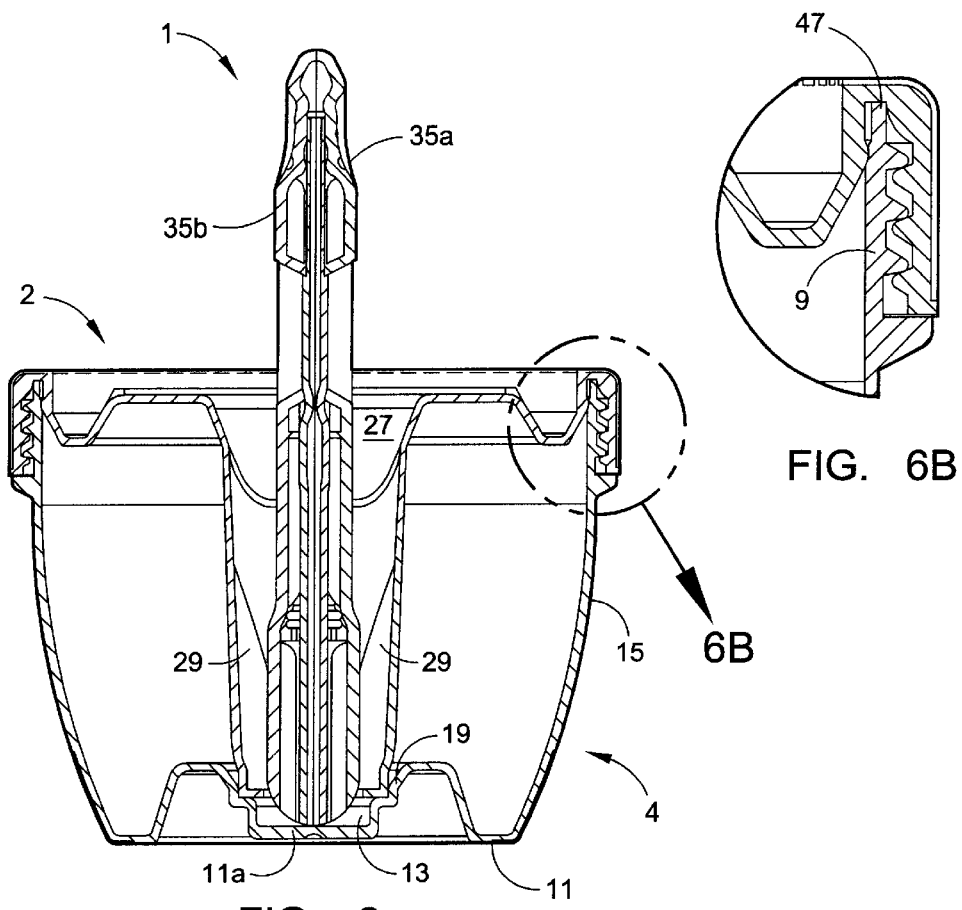
FIG. 6
FIG. 6B
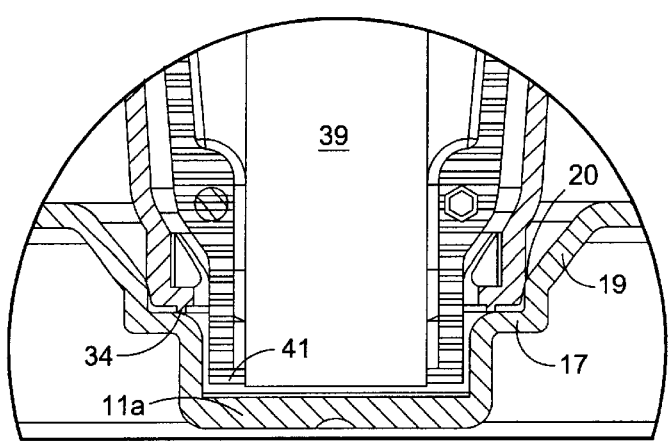
FIG. 6A

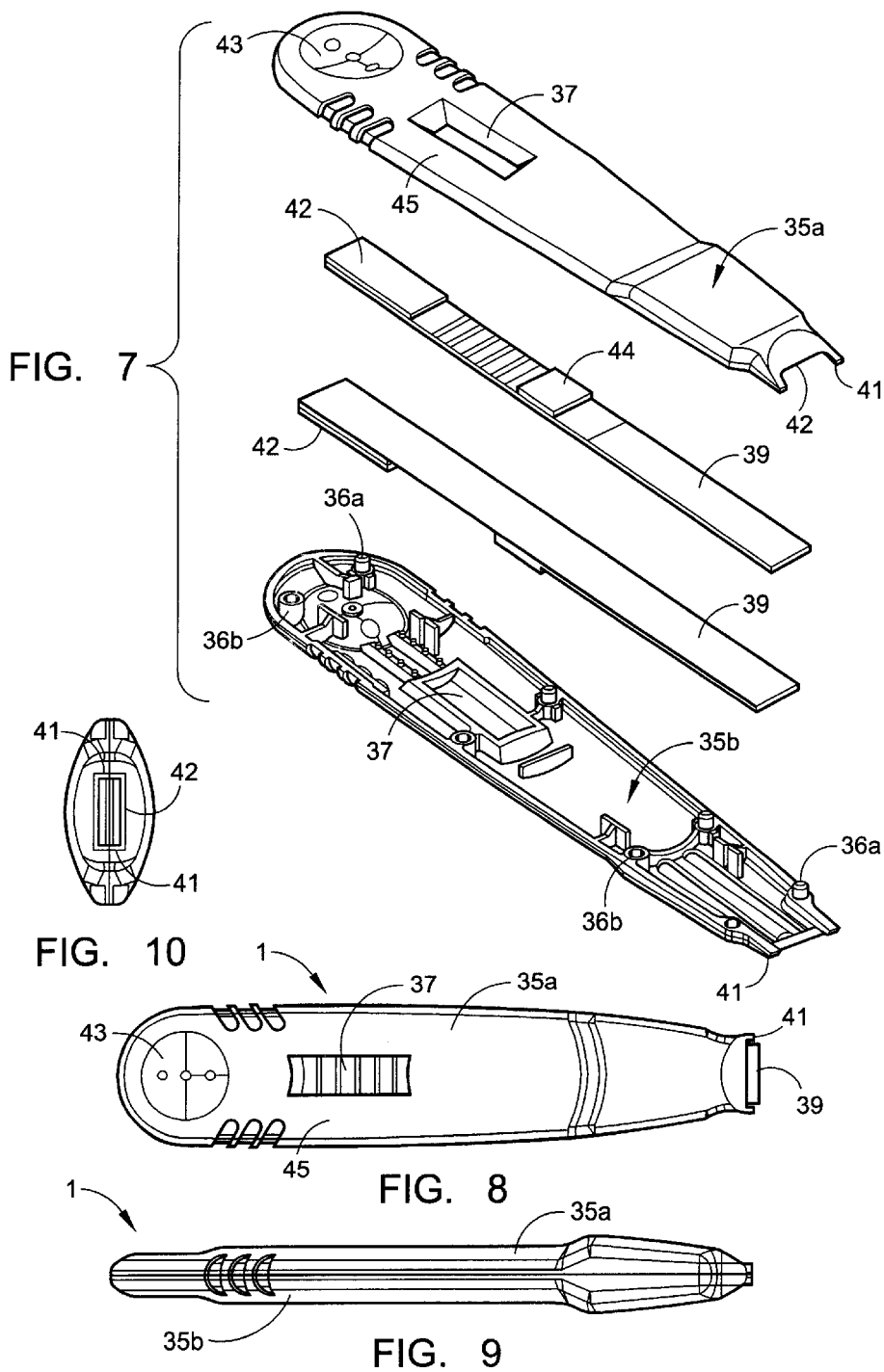

URINE TEST DEVICE

FIELD OF THE INVENTION

This invention relates to devices for collecting, testing and transporting liquid biological specimens of bodily fluids, such as urine, and methods for testing such a specimen. More particularly, the invention relates to disposable containers for collecting liquid specimens that are capped following collection, the design of which facilitates accurately testing a portion of the collected sample at the container, without removing the cap, in a manner so that the remainder of the sample remains unadulterated and can be shipped to a laboratory or the like for controlled testing to confirm the initial test results.

BACKGROUND OF THE INVENTION

Testing of bodily fluid specimens, such as urine, has become well known in today's society, but such testing has frequently exposed the tester to contact with such bodily fluid, either necessarily or inadvertently, while carrying out such a test procedure. Moreover, there is often a need, as in hospital emergency rooms or the like, to carry out such tasks quickly, and such may have a further propensity for exposure of the tester.

A number of approaches have been made as potential solutions for this problem. For example, U.S. Pat. No. 5,976,895 shows a drug abuse test kit wherein a cup for holding the urine specimen has a threaded upper edge and is fitted with an inner closure insert once the sample is in place. The insert has a diametrical slit through which a multiple drug test card, carrying a plurality of immunoassay test strips, can be slid before a screw cap or closure is threaded into place to close the container. The visual end points of the test strips are viewed through the transparent container wall; however, the entire sample remains in contact with the test card raising the possibility that some contamination from the test card could occur during transporting to an analytical laboratory whenever confirmatory testing would be performed under highly controlled conditions.

U.S. Pat. No. 5,119,830 shows a device where an analytical specimen cup is fitted with a specialized cap that can be secured to the container by the donor so that the person monitoring the testing need not be at all exposed, as they will be handed a closed container. The specialized cap is then manipulated to break a frangible barrier that opens a compartment in the cap to communicate with the cup containing liquid specimen; thereafter, inversion of the cup fills the lid compartment and contacts a test strip with the specimen, causing the immunoassay to be carried out, with color change being viewed through the transparent upper flexible sheet carried by the lid.

A number of other variations of this type of device have been designed where a specialized cap is provided with assay test strips and with a valve of some type that can be manipulated while the cup remains closed and thus cannot contaminate the person carrying out the test. Devices of this type are shown in U.S. Pat. Nos. 4,690,801; 5,429,804; 5,501,837; 5,591,401; and 6,074,606. Test devices of the same theme have been developed to fit with a rectangular container where the lid is of two-part construction, interconnected by a living hinge; chemical test strips are provided in a test space located in a compartment on the underside of the inner cover into which the specimen can pass once a frangible closure is broken, as shown for example in U.S. Pat. No. 5,640,969 and 5,882,600. In another variation on this theme, U.S. Pat. No. 6,168,758 shows a specialized cap which is threaded onto a cylindrical specimen cup and includes a plurality of chromatography strips which will visually display the assay result. Once the cap is secure, the container is inverted causing a reservoir underside of the cap to fill and collect a predetermined volume of the liquid specimen with the specimen being transmitted via wicking. During the filling of the reservoir, the intention is that a valve member will automatically swell, by absorption of liquid, and eventually close the passageway so that there will no longer be communication between the filled reservoir and the remainder of the specimen sample in the container itself. A further variation on this theme is shown in U.S. Pat. No. 5,403,551 where, instead of locating the assay test elements on the underside of the cap, they are located in a separate chamber constructed in the side wall of the specimen container itself, having an entrance opening near the very top thereof. Once the donor has contributed the specimen, a screw-on cap is applied, and through rotative positioning of the cap, a valve leading to the side wall chamber can be opened or closed. By opening the valve and inverting the cup, the reservoir in the side chamber can be filled with a sample of the specimen while the cap remains in an essentially closed condition. The results of the testing can be observed through the transparent side wall of the chamber or the like. A device shown in U.S. Pat. No. 4,473,530 is generally similar.

More recently, a primary concern with testing of urine samples or the like is to assure that, when an initial test is run, no back contamination can potentially occur between the materials used in such initial test and the remainder of the untested specimen in the cup or container. U.S. Pat. No. 4,109,530 shows a liquid specimen transfer container that is designed to provide two interconnected storage chambers in order to avoid cross-contamination therebetween. U.S. Pat. No. 5,897,840 applies this concept to a multi-chambered urine specimen container wherein the interconnection of a specialized cap with a depending tubular wall segregates two concentric chambers. The central chamber is provided with a septum through which a hypodermic needle can be inserted to extract a sample, and the outer chamber is emptied via an integral upstanding spout formed near the periphery of the cap, the tip of which can be cut off by a pair of scissors.

U.S. Pat. No. 4,927,605 shows a somewhat more complicated specimen collection container wherein the lid is placed atop the cup holding the urine sample. One or more evacuated tubes are opened through the use of hollow needles and allowed to fill with a portion of the urine sample, which tubes can then be removed from the chamber by peeling off a flexible cover to expose a removal opening. In several alternative embodiments, an isolatable chamber is provided in the lower portion of the specimen-collecting cup which has an opening that is automatically closed by the application of the cap or lid, allowing the segregated chamber to be accessed through a side sample port that will allow withdrawal of the sample from the subchamber to an appropriate testing vessel while preserving the major portion of the collected specimen without potential contamination as a result of the withdrawal of the sample from the segregated subchamber.

Although many of the foregoing devices, if handled precisely as intended, could provide for adequately testing a sample of a liquid specimen without exposing the tester to the specimen and in a manner so that there would be very little potential for contamination or adulteration of the remaining sample as a result of contact with, and particularly prolonged contact with, the assay materials themselves; however, the foregoing presupposes complete training of all testing personnel to precisely carry out the assay and presupposes the careful attention of each person to such details. In a imperfect world, solutions to this problem have continued to be sought, particularly ones that would simplify the procedure and the construction of such devices. Overall, better solutions are sought which will eliminate any possibility of tampering with the assay by the donor, i.e. by the donor never having possession of the testing mechanism, and in which a sealed container is simply supplied to the monitor/tester who can immediately and simply carry out an initial accurate test in a manner that positively avoids cross contamination with the remainder of the specimen.

SUMMARY OF THE INVENTION

The invention provides a device for collecting, testing and transporting a liquid sample of bodily fluid, e.g. a urine specimen or the like, which is simple in construction and economical to manufacture, which avoids potential adulteration of the main portion of the specimen by possible intercommunication with the test materials and which segregates a liquid sample of defined volume from the remainder of the liquid specimen in a manner in which it can be initially tested at the container without danger of exposure to the tester. The device utilizes a container or cup designed to provide a main chamber for storing the bulk of the liquid specimen, which has a subchamber formed in its bottom wall. It is used in combination with a lid for closing the upper opening into the cup, which lid is constructed with a depending hollow tube section that includes an initially closed aperture at its terminus. The device is used in combination with a test element or cartridge that is proportioned for insertion of its lower end through this aperture into this subchamber. The depending hollow tube section has a lower end which seals with an interior wall of the subchamber and thereby isolates a defined volume of liquid within the subchamber from the remainder of the liquid specimen in the container. The test cartridge has a casing which is assembled from two of the same parts that snap together as mirror images. Its bottom end opens the closed aperture at the terminus of the hollow tube section and slides through it while mating with the bottom section of the interior of the hollow tube to allow controlled leakage therepast. A wicking arrangement then transfers the defined volume of liquid from the subchamber to an assay strip which provides a response that is detectable exterior of the container, as through a window in a region of the test cartridge casing that extends above the lid. This arrangement allows initial testing to readily be carried out at the container by simply inserting the test cartridge so that it splits and passes through the frangible seal, while eliminating the possibility of cross contamination of the remainder of the specimen.

BRIEF DESCRIPTION OF THE DRAWINGS

FIG. 2 is a front view of the device illustrated in FIG. 1 with the lid installed in place upon the cup;

FIG. 3 is a sectional view taken along the line 3—3 of FIG. 2.

FIG. 3A is a fragmentary enlarged bull's-eye view of a portion of the view of FIG. 3 indicated by the circle;

FIG. 3B is a sectional view, similar to FIG. 3A, of only the bottom portion of an alternative embodiment of a lid.;

FIG. 6 is a side sectional view taken 90° from the section of FIG. 5;

FIGS. 6A and 6B are enlarged fragmentary views similar to FIG. 3A of the circled sections of FIGS. 5 and 6;

FIG. 7 is an exploded perspective view of the test cartridge;

FIG. 8 is a front view of the test cartridge;

FIG. 9 is a side elevational view of the test cartridge of FIG. 8;

FIG. 10 is a bottom view enlarged in size of the test cartridge of FIG. 8;

DETAILED DESCRIPTION OF THE PREFERRED EMBODIMENT

The present invention provides a device for collecting, testing and transporting a liquid sample of bodily fluid, e.g. a urine specimen or the like, which is simple and straightforward to use and which isolates the technician carrying out the test from any contact with the specimen while at the same time segregating a sample of the specimen to be initially tested from the remainder of the specimen so that any potential cross-contamination is positively avoided. Moreover, the design of the device is such that a defined volume of test sample is segregated from the remainder of the sample for use in the initial test, and the entire amount of this test sample is absorbed into the test cartridge by wicking so there is no liquid left exterior of the sealed portion of the cup to possibly affect the technician after the test has been completed.

Figure 1:
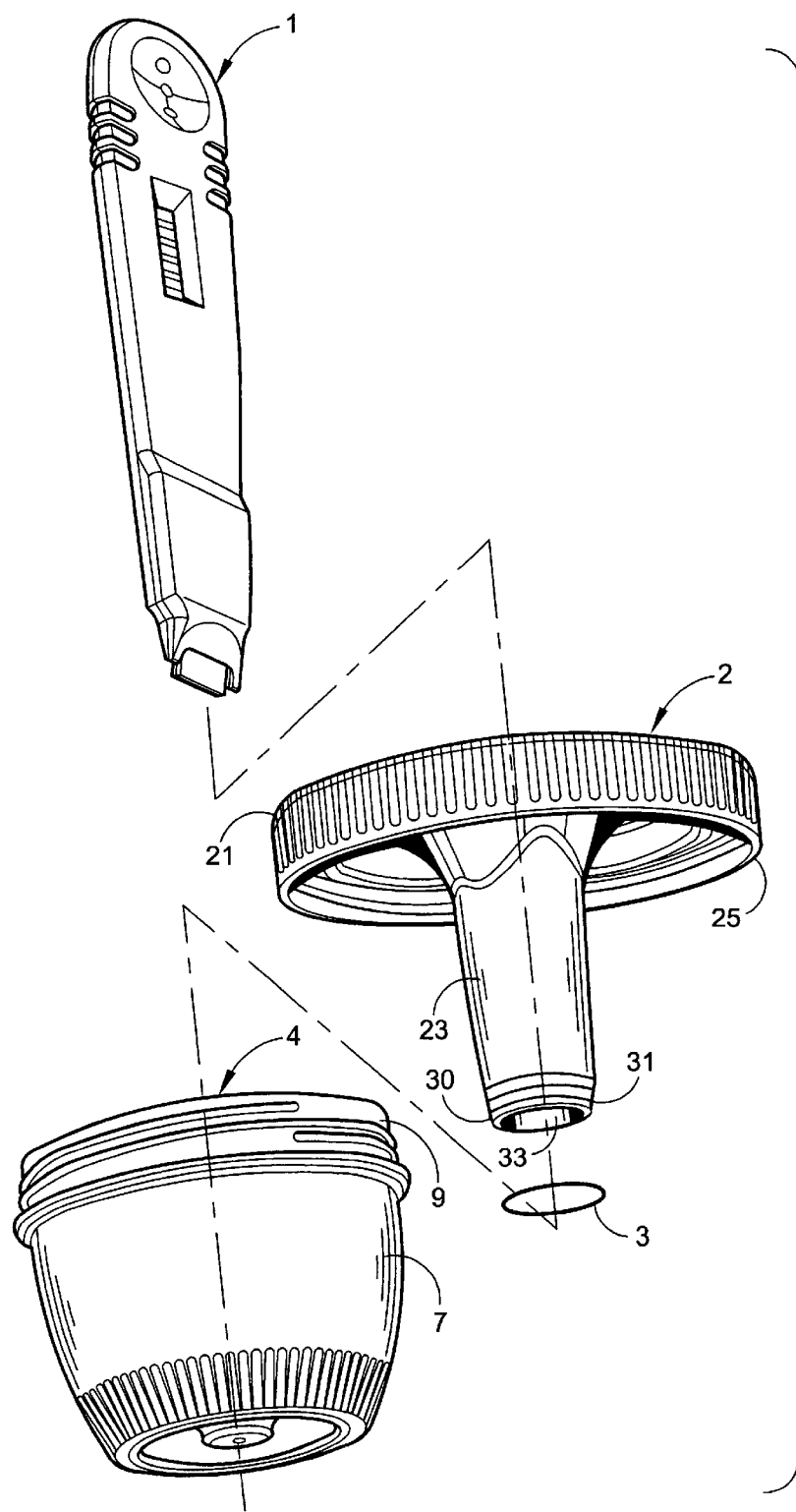
FIG. 1 is an exploded perspective view showing a bodily fluid test device embodying various features of the invention with the lid separated from the cup.
Figure 4:
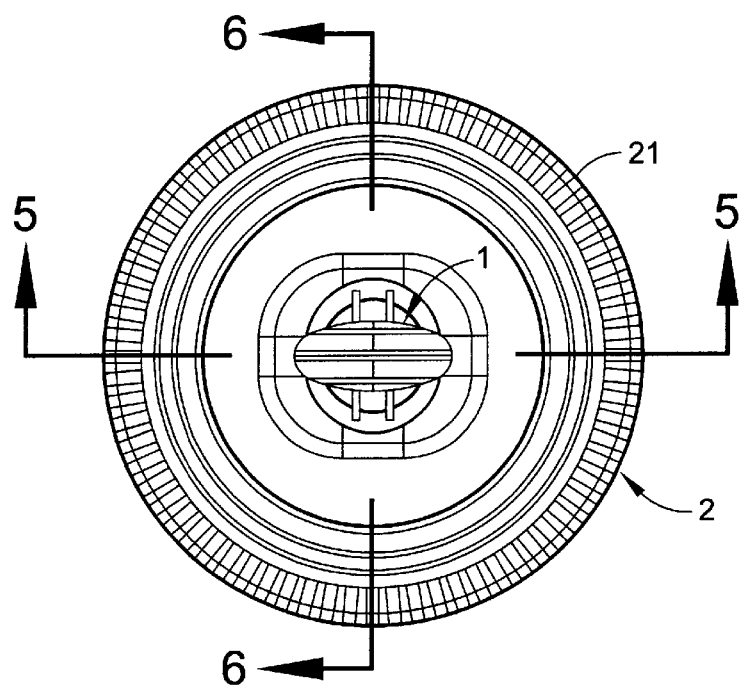
FIG. 4 is a top view of the test device of FIG. 1 with a test cartridge installed in test position.
Figure 5:
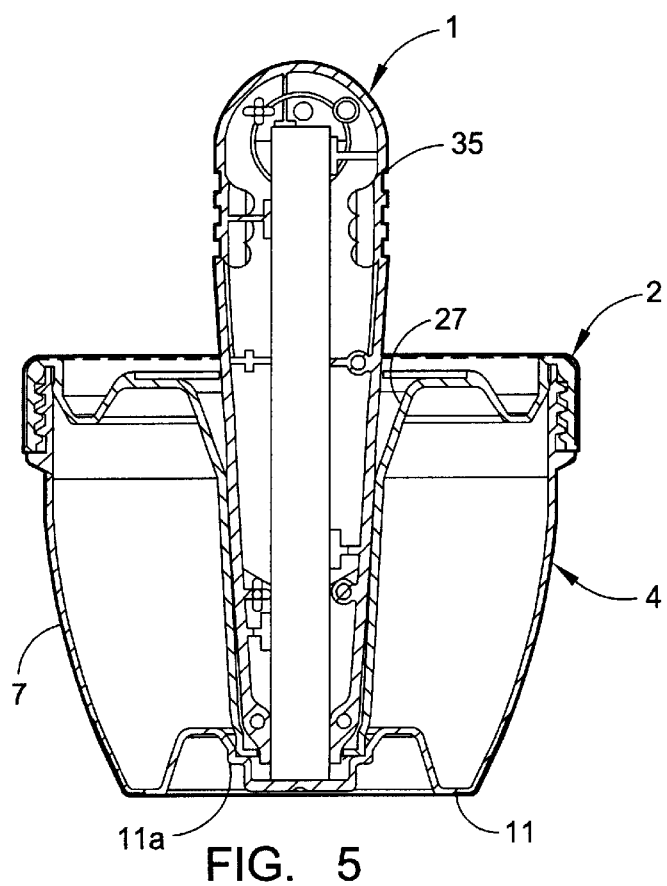
FIG. 5 is a front sectional view taken generally along the line 5—5 of FIG. 4.

One embodiment of the invention shown in FIG. 1 includes a test element or cartridge 1, a lid 2, a frangible circular liquid-impervious seal 3 for sealing a bottom surface of the lid, and a cup or container 4 for collecting the liquid specimen. As best seen perhaps in FIGS. 4 and 5, the cup 5 is formed with a sidewall 7 of generally arcuate, frustoconical or cylindrical shape which terminates in an upper rim section 9 having a cylindrical exterior surface. Preferably, a set of male threads are provided on this exterior surface for mating with cooperating female threads on the lid 2; however, if desired, a bayonet-type fitting or female threads on the interior surface of the rim section 9 might alternatively be employed.

The cup or container 4 is preferably injection-molded from polymeric material such as polystyrene, polyethylene, polypropylene, ABS or the like, with polypropylene being preferred. As a result, the container 4 is of one-piece construction with the sidewall 7 being integral with a bottom wall 11. A central section 11a of the bottom wall 11 is integrally molded so as to create an upwardly open subchamber 13 of defined volume that is centrally located and created by a sidewall 15 of circular cross-section that extends generally upward in two steps 15a and 15b from the very center of the cup so that the subchamber is concentric with the bottom wall 11 of the cup. The sidewall 15 is formed with a shoulder 17 that provides a flat horizontal intermediate surface lying between the two steps 15a and 15b, with the sidewall preferably being of right circular cylindrical shape below the shoulder and immediately above the shoulder; however, it terminates at its upper end with a flaring frustoconical section 19. An interior transition edge 20 is located at the junction of the upper step 15b and the flaring section 19.

The lid 2 is formed with an upper cap portion 21 and a depending hollow plug section 23. The lid 2 is also preferably injection-molded from any of the plastics mentioned above so as to also be of one-piece construction, with polyethylene presently being preferred. The cap portion 21 is of generally annular shape being open in its center through the interior of the hollow plug section 23 and having a peripheral depending flange 25 that carries female threads or the like on its interior surface that will mate with the threads on the rim section 9. The hollow plug 23 is frustoconical in shape throughout most of its length, having an outwardly flaring entrance section 27 in the upper region of the lid 21 and a plurality of tapered guide fins 29 near the lower end of the interior surface that lead gradually inward to the central aperture 28. As best seen perhaps in FIG. 3A, the exterior of the plug section 23 has a waist section 30 of reduced diameter that then terminates in a frustoconical terminal surface 31 leading to a generally flat bottom wall 33 (FIG. 1) that is centrally open. The apertured bottom wall 33 may have a circular shape with the central aperture 28 that is temporarily sealed by a thin circular, frangible, liquid-impervious, sheet material disk 3, which is attached using a suitable adhesive or the like. The disk can be made of any suitable liquid-impervious material that is readily frangible; while a metal foil, e.g. aluminum, is preferred, appropriate plastics which can be easily split or fractured can instead be used. Preferably, the disk is formed from aluminum foil which is coated on at least its upper surface with a low strength thermoplastic polymer, such as polyethylene, which facilitates heat-sealing of the disk to the bottom surface 33 of the hollow plug section 23.

To facilitate heat-sealing, the otherwise flat bottom surface 33 is preferably formed with a thin encircling ridge 34 which surrounds the aperture 28 and tends to focus the heat, as well known in this art, during heat-sealing and assure that there is a strong 360° seal in at least the region of the ridge. The aperture 28 has the general shape of the exterior of the bottom of the cartridge that will pass therethrough, and the ridge 34 is preferably located uniformly a short distance e.g. 0.02 in., from the edge thereof. The ridge 34 is depicted in FIGS. 3A and 6A for example, and although parts of the seal are not shown to be in tight contact with the undersurface of the hollow plug, it should be understood that these regions would be filled in by polyethylene that has flowed thereinto during the heat-sealing process. Furthermore, to avoid any tolerance problems, the outer diameter of the circular seal might be about 0.050 to 0.060 inch less than the outer diameter of the hollow plug at its terminus. The location of the ridge 34, close to the edge of the aperture 28, minimizes the extent the foil can deflect when the cartridge enters and thus minimizes potential spraying at the instant of entry.

When the lid 2 and the cup 4 are first assembled, after the liquid sample has been received, the frustoconical upper entrance section 19 above the subchamber serves to smoothly guide the hollow plug into position. The perimeter of the foil disk 3 will generally be spaced slightly above the horizontal surface provided by the shoulder 17, and the frustoconical terminal end 31 of the hollow plug section 23 will be in loose engagement with the transition edge 20. Relative clockwise rotation of the lid 2 causes the male and female threads to interengage and drives the hollow plug section further into the upper region of the subchamber 13. This results in the creation of an interference or press-fit, i.e. friction seal, at the location of the transition edge 20 which tightly seals the liquid-filled subchamber 13 from the liquid in the rest of the cup. The foil disk 3 may touch the flat surface of the shoulder 17 or be spaced very slightly therefrom.

FIG. 3B illustrates an alternative embodiment which the bottom end of the hollow plug section of the lid may have; it is illustrated using prime numbers to reference the corresponding structure hereinbefore described with respect to FIG. 3A. Shown is a fragmentary view of a hollow plug section 23' which includes a similar waist section 30' of reduced diameter, below which there is disposed a terminal wall surface 31' that extends downward to a circular bottom wall 33' wherein a similar aperture 28' is centrally located. The otherwise flat bottom surface of the wall 33' carries a similar ridge 34'. The difference between the lower end of the hollow plug section 23' and the section 23 previously described lies in the wall surface 31' which, instead of having a primary frustoconical surface where the seal occurs, has a primary right circular cylindrical surface with only a very short, "leadin" chamfered surface 31a'. As a result, a seal is generated over a finite length between the right circular cylindrical surface 31' and the interior right circular cylindrical surface of the upper step sidewall of the cup 15b, and the tolerances of these two molded polymeric parts are set so as to create an interference of between about 0.001 and 0.005 in. There is sufficient flexibility in molded polyethylene and polypropylene parts to stretch/compress so as to create such a tight interference fit, and the chamfered terminal edge 31a' of the hollow plug section assures ready alignment of these two surfaces of similar diameters.

The cartridge 1 includes an elongated outer holder or casing that is preferably formed from two halves 35a and b which may be of identical construction and which are designed to snap together as a result of the mating of interengaging parts. For example, as seen in FIG. 7, each of the halves on its interior side may, as depicted for 35b may have a series of outstanding posts or pegs 36a along one edge and a series of receptacles 36b for receiving such posts molded along its opposite edge so that when the other half is reversed, see 35a, the rear surfaces will present the mirror image of each other, and the two halves of the cartridge will snap together. This utilization of two identical pieces provides substantial cost savings by requiring only a single injection mold and reduction in inventory of parts. The construction of each holder half 35 is such so as to provide a viewing window 37 through which the results of the immunoassays can be viewed after the test has been completed, and they define a central channel, aligned with the windows that will receive two flat immunoassay test strips 39. While two strips are preferred for simplicity of construction of the holder, three or more strips might be included in an appropriately designed cartridge, as mentioned hereinafter. The strips 39 can be of the standard form used in the industry and can be made of a nitrocellulose or other suitable material having a pore size that will serve to wick, by capillary action, a liquid that is applied to it causing same to travel along its entire length. The two strips 39 are juxtaposed back to back, and the rear surface of each may include a sheet of thin backing material as well known in the art. Spaced-apart zones along the length of each strip are impregnated with specific antibodies or antigens having a specificity for a particular compound, for the presence of which the test is to be conducted. Each antibody or antigen will bear a visible label, for example a dye sol or colored latex particles that will produce a color change.

The bottom right-hand edge (when viewed from the exterior surface) of each half 35 of the holder is preferably provided with a protruding chisel point 41 located adjacent a recess 42 which provides one-half of the open rectangular port in the assembled cartridge. As a result, in the illustrated snap-together cartridge 1, there will be a protruding chisel point 41 along each side edge, flanking the open port. These protruding chisel edges 41 are designed to penetrate the foil with minimal force and then split the foil lengthwise in the direction across the cartridge and allow the terminal end of the cartridge to readily pass through the region of the seal and move downward until it engages the bottom wall 11a at the center of the container. Alternatively, a breakaway plastic seal similar to those commonly found on lids for soft drink cups, that easily rupture to allow the insertion of a straw, might be employed instead of the foil seal. Another alternative is to press-fit a shaped plug to completely fill the aperture which is then pushed out as the cartridge is inserted.

Figure 10A:
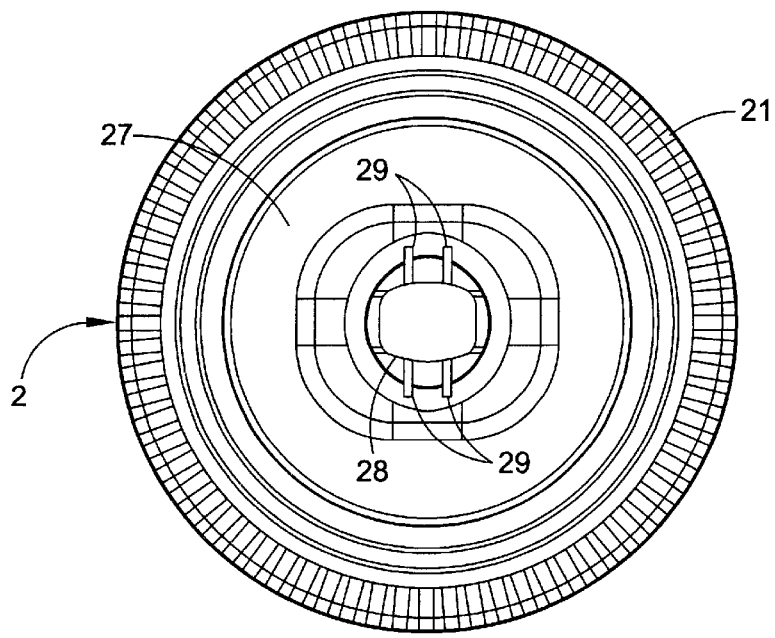
FIG. 10A is a top view, reduced in size, of the lid of FIG. 1.

As best seen in FIG. 10, the cross-section of the cartridge 1 is generally elliptical with flattened ends, and the lower end replicates this shape of proportionately lesser dimensions. The interior guide fins 29 (FIG. 6) of the hollow plug are constructed so as to taper, from the circular cross-section in its upper region to a mating generally elliptical cross-section in its terminal portion leading to the generally elliptical aperture 28, best seen in FIG. 10A, to provide a region which is designed to receive and laterally support the lower end of the cartridge 1. As a result, the juxtaposition of the front and rear surfaces of the cartridge and the lower sections of the guide fins 29 in the interior of the hollow plug section assures that the cartridge will stand vertical within the assembled lid and cup. The immunoassay strips 39 are dimensioned so as to extend downward and slightly out of the snap-together cartridge halves 35 through the port 42, so as to protrude into the region between the chisel points 41 and thus come into contact with and absorb the liquid in the defined volume of the subchamber 13.

In operation, the cup 4 is used to collect a specimen, as for example by giving a cup and lid combination to a donor or other e.g. an athlete or the like, and asking that person to provide a urine sample and then carefully screw the lid in place after the specimen is present in the cup. When the combination of specimen-carrying cup and lid is returned, the technician turns the lid 2 clockwise to be certain that it is tightly sealed to the cup 4, and this relative rotation of the mating threads causes an interference fit to be established between the terminal outer surface 31 of the hollow plug and the subchamber sidewall, e.g. at the transition edge 20, creating a tight seal between the outer surface of the hollow plug section and the interior sidewall of the subchamber, as well as at the rim 9 of the cup. As a result, a segregated sample of the specimen of defined volume is automatically isolated in the subchamber 13, and the subchamber is positively sealed off from the remainder of the specimen contained in the outer annular region of the container because of the seal at the outer surface of the hollow plug. The sealed cup would then be appropriately labeled and transferred to a technician for the initial testing.

The technician would then take a cartridge 1 containing immunoassay or other strips designed to test for a desired substance or group of substances, grasping it at depressions 43 formed at the top portion of the cartridge and inserting it downward into the interior of the hollow plug section 23 of the lid. When the terminal end of the cartridge engages the inwardly flaring guide fins 29, it is automatically aligned, and the mating, generally elliptical cross-section bottom portion is automatically aligned with the aperture 28. Continued downward vertical movement causes the chisel points 41 to puncture the frangible thin metal foil seal 3, splitting the seal across the center region and permitting the lower end of the cartridge to protrude into the liquid that fills the subchamber 13. While a small amount of liquid may be displaced upward between the edge of the aperture 28 and the cartridge casing, where a clearance of about 0.003–0.005 in. is provided. As a result, the bottom ends of both strips 39 will be immersed in the liquid sample that fills the subchamber, and any displaced liquid quickly drains back as liquid is absorbed in the cartridge. Liquid is quickly absorbed at the bottom end of the cartridge where the strips protrude and then rises by capillary action to the upper end of each test strip where a sink pad 42 is preferably provided as well known in this art. One or more separate lower zones 44 are preferably provided wherein the rising liquid can bind to a labeled reagent if a particular ligand is present which will then be carried with it to the various indicator band or bands that are located at the window 37. Tests for different substances would normally be incorporated into each of the test strips, and each holder is formed with a flat region 45 to the left of the window upon which an identifier will be printed to indicate the substance for which that section of the test strip will be testing. If positive, the test result will appear either as the presence of a line or the absence of such a line, as appropriate for the particular immunochromatic cartridge being used, and will be visible through the aligned section of the window 37.

In any event, the capacity of the two strips 39 plus any sink pad 42 that might be provided at the very top will be adequate to assure the absorption of all of the defined volume of the specimen sample that will have been segregated in the sealed subchamber 13. Accordingly, when the cartridge 1 is removed from the associated lid 2, the subchamber 13 that was previously filled with the specimen sample is now essentially dry and will not pose a potential hazard to the technician. At the same time, the remainder of the specimen stays sealed in the assembled lid and cup as a result of the combination of the central annular seal at the transition edge 20 and the peripheral seal, preferably at the top edge surface 47 of the cup 4 (see FIG. 6B) provided by the mating threads along the rim 9 of the cup. Accordingly, the sealed cup and sample can be transported to an authorized laboratory for testing without fear of any potential contamination having occurred as a possible side effect of having conducted the preliminary test using the immunoassay cartridge 1. Because it will be desirable to remove the cartridge 1 before sending the sample-containing cup to a testing laboratory, following cartridge removal, the technician will generally apply an appropriate circular label 47 to the lid, as shown in FIG. 3, so as to prevent any foreign matter from inadvertently entering the hollow plug section 33 of the lid.

Figure 11:
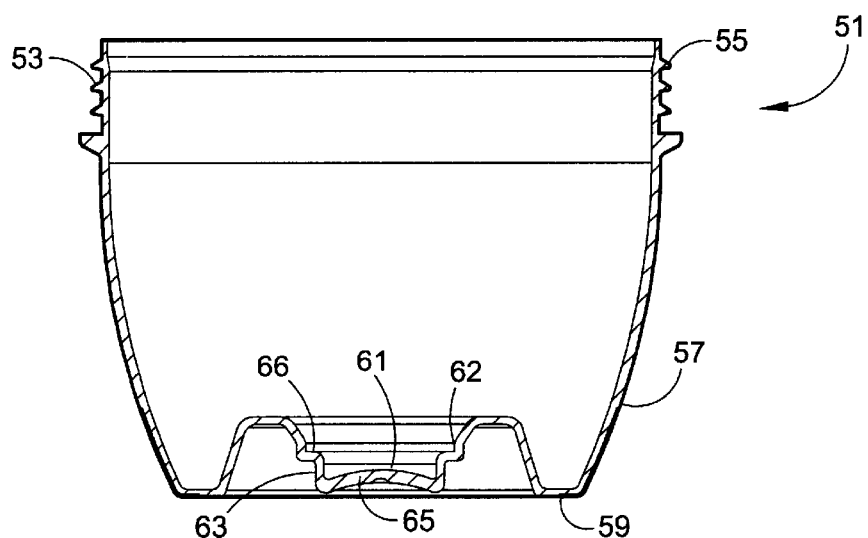
FIG. 11 is a sectional view of an alternative embodiment of a cup that might be employed in the urine test device of FIG. 1.
Figure 12:
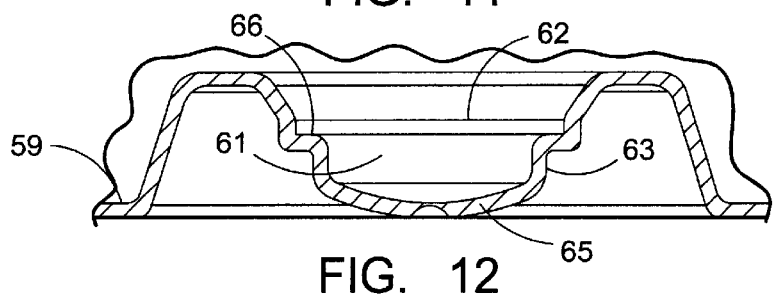
FIG. 12 is an enlarged fragmentary view of a portion of the cup of FIG. 11 shown in a different orientation.

Illustrated in FIGS. 11 and 12 is a cross-sectional view of an alternative embodiment of a cup 51 which might likewise be made by a suitable injection-molding process. The cup 51 has an upper cylindrical rim section 53, which is formed with male threads 55, and an arcuate or frustoconical sidewall 57 that extends downward from the rim section 53 to a bottom wall 59. The bottom wall has integrally formed therein a subchamber 61 that is created by a sidewall 63, similar to the sidewall 15 previously described, that has formed therein a transition circular interior edge 62. However, a central section 65 of the bottom wall, that forms the bottom of the upwardly open subchamber 61, is molded so as to be slightly thinner than the remainder of the bottom wall and to be concave upward, as shown in FIG. 11. Because of its relative thinness, it is capable of flexing so as to deflect over center and assume a concave upward configuration as depicted in fragmentary view FIG. 12. In operation, when the bottom end of the cartridge 1 is caused to split open the frangible sheet material seal residing just above or at the horizontal intermediate shoulder 66 and protrude downward into the subchamber 61, some of the liquid in the subchamber 61 will be initially displaced as other of the liquid is wicking into the porous nitrocellulose strips. Rather than have some liquid be possibly displaced upward between the exterior surface of the cartridge and the interior surface 63 of the hollow plug, the overcenter flexing of the circular bottom wall portion 65 creates an open region that slightly enlarges the subchamber 61 and momentarily accepts some of the displaced liquid. As can be seen in FIG. 12, the central portion 65 is located slightly above the plane of the peripheral region 59 of the bottom wall so that it just extends to, and not past, that plane once such extension has occurred. Because of the inherent memory of the polymeric material from which the cup 51 is injection-molded, once liquid has been absorbed into the strips, the pressure that caused this overcenter action will have been relieved, and the central bottom wall 65 will again assume its normal upwardly convex configuration.

Although the invention has been described so as to set forth the best mode presently contemplated by the inventors for carrying out the invention, it should be understood that various changes and modifications as would be obvious to those skilled in this art may be made without departing from the scope of the invention which is defined in the claims appended hereto. For example, the components may be made from various suitable polymeric materials, and although injection-molding is the preferred method of manufacture, other molding processes can alternatively be used. Although a snap-together two-sided holder is preferred for simplicity of construction, a triangular, or four or more sided, holder might instead be used to a accommodate three or four or more test strips. Similarly, a wide variety of chemical and/or biological assays have been performed through the utilization of porous strips of nitrocellulose or the like over the past two decades, and the invention is not considered to be limited to any particular assays or even types of assays.

The disclosures of each of the U.S. patents set forth hereinbefore are expressly being incorporated herein by reference. Particular features of the invention are set forth in the claims that follow.

What is claimed is:

1. A device for collecting, testing and transporting a liquid sample of bodily fluid or the like, which device comprises:

a container having a continuous sidewall that extends between a bottom wall and an upper opening through which a liquid specimen can be collected, said container providing a main chamber for storing such specimen and an upwardly open subchamber formed by an upstanding wall portion of said bottom wall of said container, and a lid for closing and sealing said upper opening to said container, said lid having a depending hollow plug section that terminates in a closed aperture, said terminal end of said plug sealingly interengaging with said subchamber to create a closed cavity of defined volume that is isolated from communication with the remainder of said chamber, whereby a liquid sample of defined volume is segregated from the remainder of such specimen within said closed cavity, so it can be tested without potentially contaminating the remainder of such specimen in said container by inserting a test element downward through said aperture at the terminus of said hollow plug section.

2. The device according to claim 1 wherein said subchamber is circular in cross-section and wherein said hollow plug section has an exterior surface of circular cross-section which forms a sealing press-fit with said upstanding wall of said subchamber.

3. The device according to claim 1 wherein said lid aperture is closed with a sheet material seal bonded to a bottom surface of said hollow plug.

4. The device according to claim 3 wherein said sheet material includes a frangible metal foil which is rupturable by said lower end of said test element to allow passage downward therethrough.

5. The device according to claim 1 wherein said subchamber is formed so as to have an upper frustoconical entrance positioned above a cylindrical section.

6. The device according to claim 5 wherein said subchamber includes a horizontal shoulder which extends radially inward from said cylindrical section and which is located below said terminal end of said hollow plug section when said container and said lid are assembled.

7. The device according to claim 6 wherein said opening at the top of said container sidewall is circular and contains threads surrounding said opening, and wherein said lid contains a peripheral flange formed with cooperating threads which lock said lid in sealing association with said container and prevent axial separation therefrom and which force an exterior surface of said hollow plug section into frictional engagement with an interior surface region of said subchamber.

8. The device according to claim 1 wherein said bottom wall is integral with said container sidewall and wherein said subchamber is defined by an inner sidewall of a hollow annular region that is an integral part of said bottom wall of said container and extends upward therefrom.

9. The device according to claim 8 wherein said bottom wall has a center section in the region of said subchamber that is concave upward and of a thickness so as to flex and become concave downward upon an increase in pressure in said subchamber.

10. The device of claim 1 in combination with a test element which has (a) a casing that has a lower end portion for entry into said subchamber to contact liquid occupying said subchamber, (b) said casing having a port in said lower end portion to allow entry of said liquid sample thereinto, (c) an assay arrangement within said casing, and (d) a wicking strip arrangement for transferring liquid from said defined volume of liquid in said subchamber to said assay arrangement in order to provide a response that is detectable exterior of said container.

11. The device according to claim 10 wherein said wicking strip arrangement has a capacity to absorb substantially all of said defined volume of liquid.

12. The device according to claim 10 wherein said test element is elongated and has a lower section of generally elliptical cross-section which is designed to be slid axially downward through said aperture which has a mating slightly greater shape until its lower end thereof engages the bottom of said subchamber as a result of such axial movement.

13. The device according to claim 10 wherein said assay arrangement provides a visual signal and wherein said test element casing contains a window through which said signal can be visually observed at a location exterior of said container.

14. The device according to claim 13 wherein said assay means includes chromatographic membrane material along which said liquid sample will travel by capillary action.

15. A device for collecting, testing and transporting a liquid sample of bodily fluid or the like, which device comprises:

a container having a continuous sidewall that extends between a bottom wall and an upper opening through which a liquid specimen can be collected, said container providing a main chamber for storing such specimen and an upwardly open subchamber which is a part of said bottom wall, a lid for closing and sealing said upper opening to said container, said lid having a depending hollow plug section that terminates in a temporarily closed central aperture at its lower end, said plug section, at a location near its terminus, sealingly interengaging with said subchamber to create a closed cavity of defined volume that is isolated from communication with the remainder of said chamber, whereby a liquid sample of defined volume within said closed cavity can be tested without potentially contaminating the liquid specimen in the remainder of said container, and a test element proportioned to be received within said hollow plug section for insertion downward through said aperture by opening same, which element has (a) a casing that has a lower end portion for entry into said subchamber to contact liquid occupying said subchamber, (b) said casing having a port in said lower end portion to allow entry of said liquid sample thereinto, (c) an assay arrangement within said casing, and (d) a wicking strip arrangement for transferring liquid from said defined volume of liquid in said subchamber to said assay arrangement which produces a response that is detectable exterior of said container.

16. The device according to claim 15 wherein said wicking strip arrangement has a sufficient capacity to absorb substantially all of said defined volume of liquid in said subchamber when said lid is in place.

17. The device according to claim 16 wherein said test element is elongated and has a lower section of generally elliptical cross-section which is designed to be slid axially downward through said aperture of mating shape until it is received in a bottom section of said subchamber and the lower end thereof engages the bottom of said subchamber as a result of such axial movement and wherein said hollow plug section has radial fins shaped to direct said test element casing toward said central aperture and laterally support same in substantially vertical orientation.

18. The device according to claim 16 wherein said assay arrangement provides a visual signal and wherein said test element casing contains a window through which said signal is visually observable at a location exterior of said container.

* * * * *